(12) United States Patent
Atwell

(10) Patent No.: US 9,931,156 B2
(45) Date of Patent: Apr. 3, 2018

(54) ELECTROSURGICAL INSTRUMENT

(71) Applicant: GYRUS MEDICAL LIMITED, Cardiff (GB)

(72) Inventor: Anthony Atwell, Newport (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 380 days.

(21) Appl. No.: 14/390,099

(22) PCT Filed: Mar. 28, 2013

(86) PCT No.: PCT/GB2013/050851
§ 371 (c)(1),
(2) Date: Oct. 2, 2014

(87) PCT Pub. No.: WO2013/150282
PCT Pub. Date: Oct. 10, 2013

(65) Prior Publication Data
US 2015/0057659 A1 Feb. 26, 2015

(30) Foreign Application Priority Data

Apr. 2, 2012 (GB) .................................. 1205862.4

(51) Int. Cl.
*A61B 18/14* (2006.01)
*A61B 17/29* (2006.01)

(52) U.S. Cl.
CPC ...... *A61B 18/1445* (2013.01); *A61B 17/2909* (2013.01); *A61B 18/1477* (2013.01);
(Continued)

(58) Field of Classification Search
CPC ............ A61B 18/1442; A61B 18/1445; A61B 18/1477; A61B 17/2909;
(Continued)

(56) References Cited

U.S. PATENT DOCUMENTS 4,686,963 A 8/1987 Cohen et al.
5,290,286 A 3/1994 Parins
(Continued)

FOREIGN PATENT DOCUMENTS

JP H02-55905 U 4/1990
JP H07-108045 A 4/1995
(Continued)

OTHER PUBLICATIONS

Apr. 1, 2016 Chinese Office Action issued in Chinese Patent Application No. 201380018710.0.
(Continued)

*Primary Examiner* — Jaymi Della
*Assistant Examiner* — Eunhwa Kim
(74) *Attorney, Agent, or Firm* — Oliff PLC

(57) ABSTRACT

An electrosurgical instrument for the treatment of tissue includes a longitudinal instrument shaft having a central axis, an end effector at the distal end of the shaft, the end effector including at least one element movable between a first and a second position. An actuator includes a handle which reciprocates movement between a first and second actuator position, and an actuation wire associated with the actuator for movement. Movement of the actuator causes the wire to move the element between its first and second positions, the wire running longitudinally of the shaft offset on one side from the central axis of the shaft. Compensation wire is associated with the actuator, the compensation wire running longitudinally of the shaft and being offset on the opposite side of the central axis of the shaft to that of the actuation wire.

8 Claims, 6 Drawing Sheets

(52) U.S. Cl.
CPC ............... *A61B 2017/2905* (2013.01); *A61B 2017/2912* (2013.01); *A61B 2017/2923* (2013.01); *A61B 2018/1425* (2013.01)

(58) Field of Classification Search
CPC .... A61B 2018/1425; A61B 2017/2905; A61B 2017/2912; A61B 2017/2923
See application file for complete search history.

(56) References Cited

U.S. PATENT DOCUMENTS

| | | | |
|---|---|---|---|
| 5,582,617 A * | 12/1996 | Klieman | A61B 17/29 606/170 |
| 6,171,277 B1 * | 1/2001 | Ponzi | A61B 18/1492 604/22 |
| 6,183,463 B1 | 2/2001 | Webster, Jr. | |
| 2002/0082617 A1 | 6/2002 | Nishtala et al. | |
| 2004/0015165 A1 | 1/2004 | Kidooka | |
| 2004/0158239 A1 * | 8/2004 | Behl | A61B 18/1477 606/41 |
| 2005/0222568 A1 * | 10/2005 | O'Sullivan | A61B 18/14 606/47 |
| 2008/0051631 A1 | 2/2008 | Dejima et al. | |
| 2009/0125027 A1 * | 5/2009 | Fischer | A61B 17/3203 606/46 |
| 2010/0010489 A1 | 1/2010 | Privitera et al. | |
| 2011/0071473 A1 | 3/2011 | Rogers et al. | |

FOREIGN PATENT DOCUMENTS

| | | |
|---|---|---|
| JP | H09-507149 A | 7/1997 |
| JP | H10-510169 A | 10/1998 |
| JP | 2000-210295 A | 8/2000 |
| JP | 2004-049330 A | 2/2004 |
| JP | 2007-151595 A | 6/2007 |
| JP | 2012-504016 A | 2/2012 |
| WO | WO 91/16856 A1 | 11/1991 |
| WO | 2010/039387 A1 | 4/2010 |

OTHER PUBLICATIONS

Aug. 2, 2012 Search Report issued in British Application No. 1205862.4.
Sep. 16, 2013 International Search Report issued in International Application No. PCT/GB2013/050851.
Sep. 16, 2013 Written Opinion issued in International Application No. PCT/GB2013/050851.
Jan. 10, 2017 Office Action issued in Japanese Patent Application No. 2015-503934.

* cited by examiner

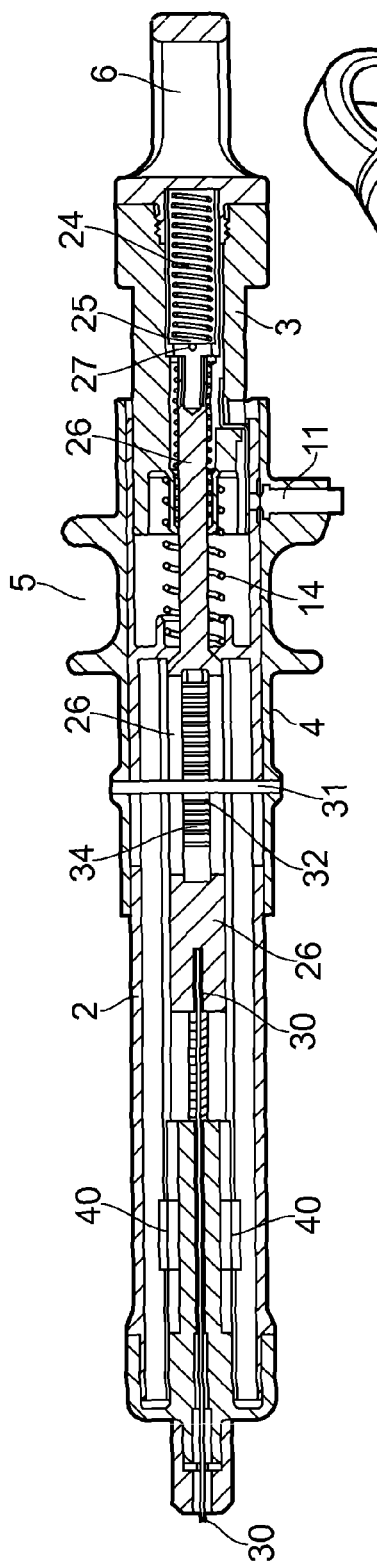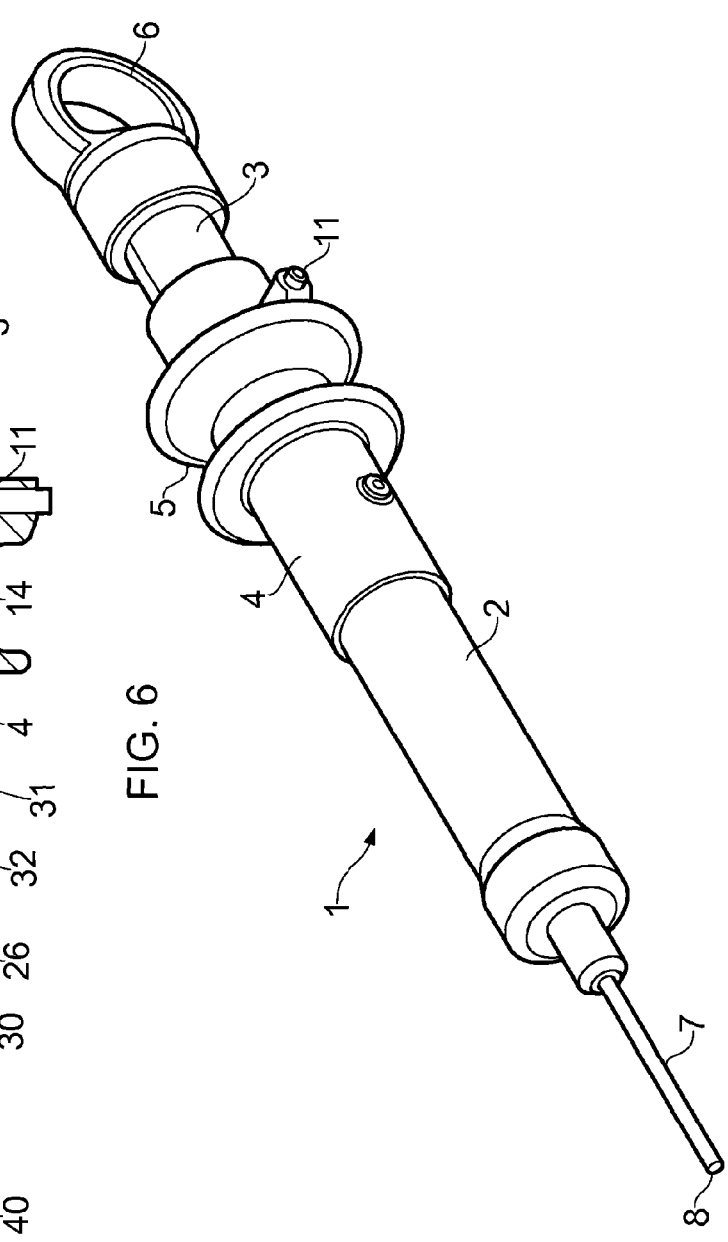

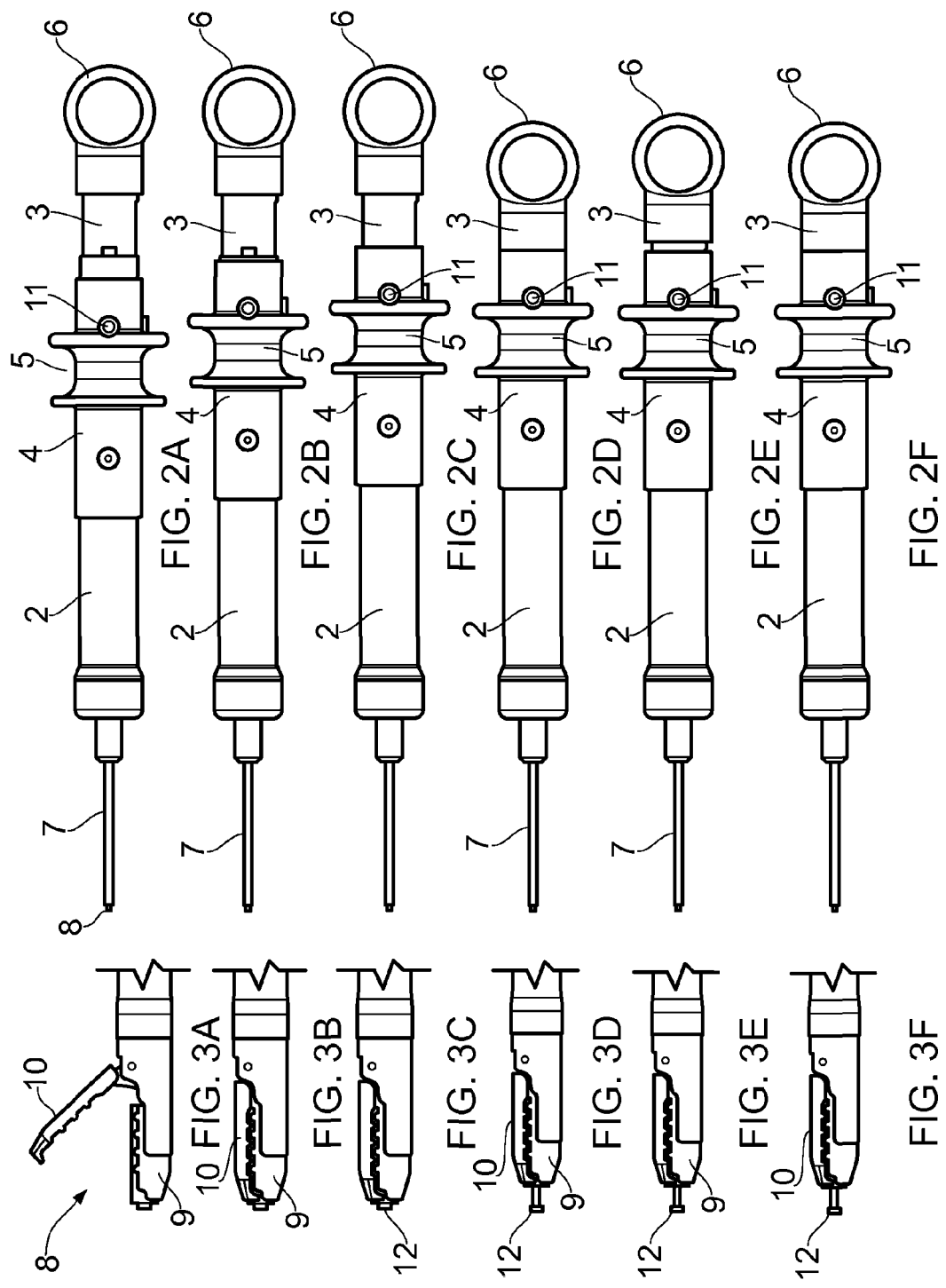

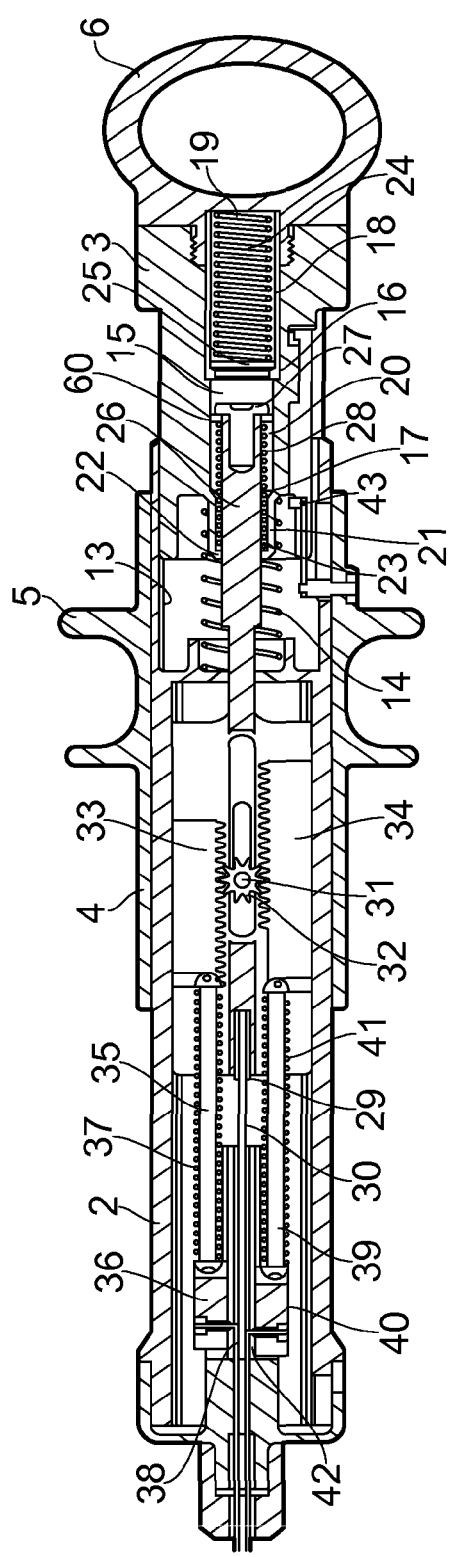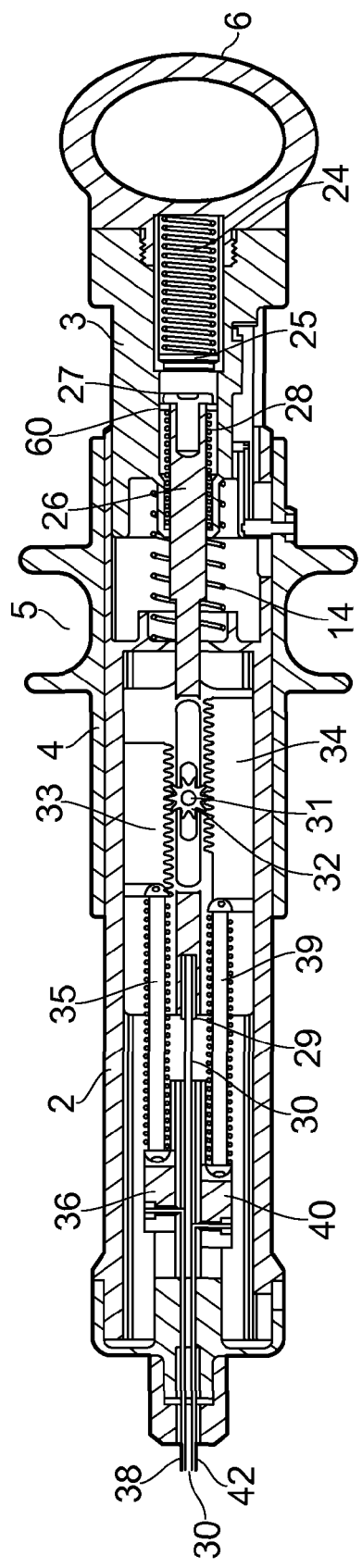
FIG. 4A
FIG. 4B

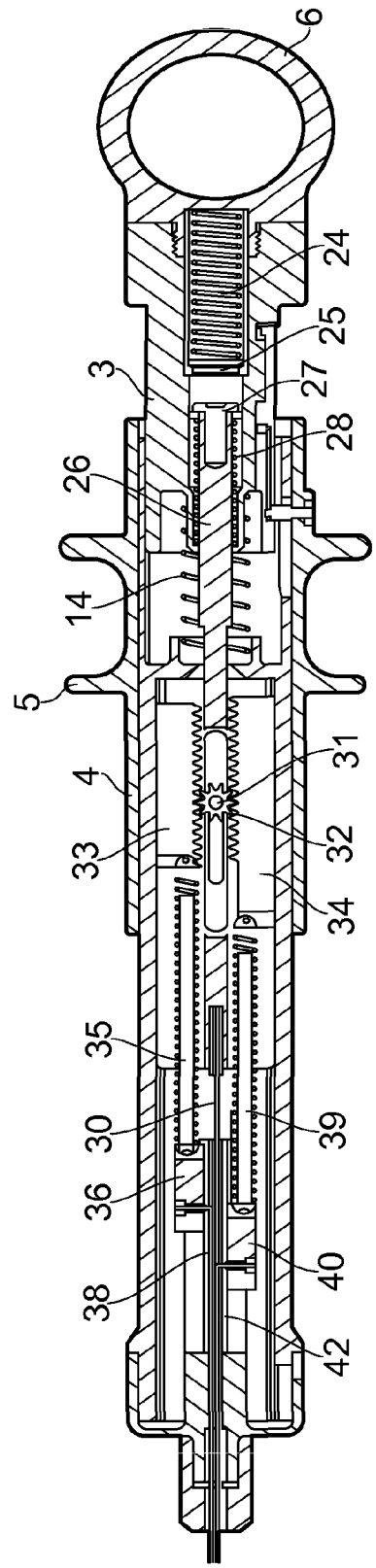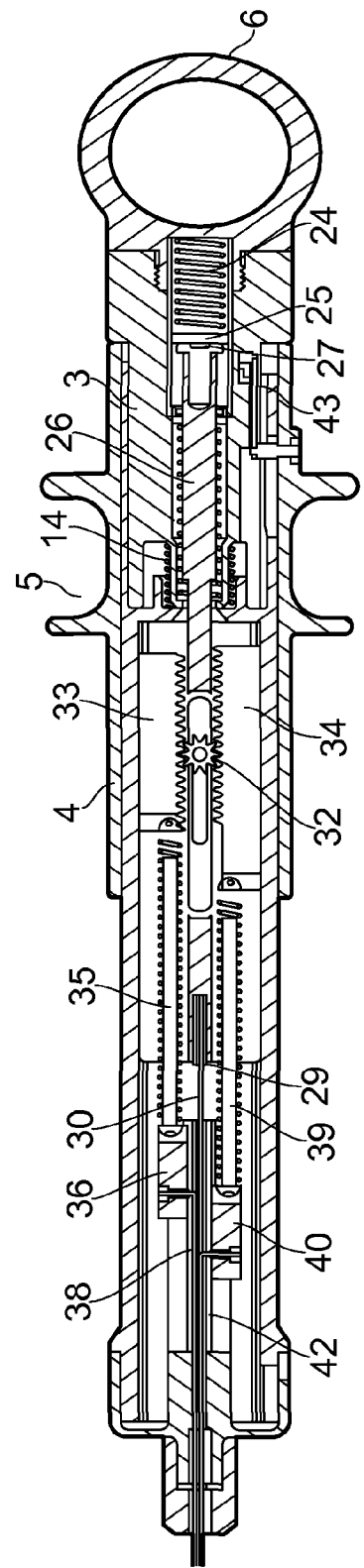
FIG. 4C
FIG. 4D

ELECTROSURGICAL INSTRUMENT

TECHNICAL FIELD

This invention relates to an electrosurgical instrument for the treatment of tissue. Such instruments are commonly used for the cutting/vaporisation and/or desiccation/coagulation of tissue in surgical intervention, most commonly in "keyhole" or minimally invasive surgery. The terms "cutting" and "vaporization" relate to the removal of tissue, whether by resection or by the volumetric removal of tissue. Similarly, the terms "desiccation" and "coagulation" relate to the creation of lesions in tissue, the necrosis of tissue, and to the prevention of bleeding.

BACKGROUND TO THE INVENTION AND PRIOR ART

Endoscopic instruments are often used in gastroenterology or cardiac surgery, and such instruments are normally introduced through an endoscope working channel, with the endoscope in turn introduced through a lumen within the patient's body. These instruments are therefore of a relatively small size, often no more than 5 mm in diameter. They are deployed at the end of a relatively long flexible shaft, such that they can be maneuvered within a lumen as described above.

Where such instruments include the deployment of one component relative to another, such deployment is often carried out by sliding one handle component relative to another. The components are often supplied with loops or moulded surfaces adapted to be contacted by the fingers and thumb of the user of the instrument. One instrument of this type is described in U.S. Pat. No. 5,290,286 in which a component is movable within a housing, the movable component being provided with a thumb ring and the housing with finger loops. The present invention attempts to provide an improvement to endoscopic instruments of this type.

SUMMARY OF THE INVENTION

Accordingly, an electrosurgical instrument for the treatment of tissue is provided, comprising i) a longitudinal instrument shaft having a central axis, ii) an end effector at the distal end of the shaft, the end effector comprising at least one element movable between a first and a second position, iii) an actuator including a handle capable of reciprocating movement between a first actuator position and a second actuator position, iv) an actuation wire associated with the actuator for movement therewith and being connected to the end effector such that movement of the actuator causes the actuation wire to move the element between its first and second positions, the actuation wire running longitudinally of the shaft and being offset on one side from the central axis of the shaft, v) a compensation wire also associated with the actuator and connected to the end effector, the compensation wire running longitudinally of the shaft and being offset on the opposite side of the central axis of the shaft to that of the actuation wire, and vi) a force balancing mechanism allowing relative movement between the actuator and one or both of the actuation wire and the compensation wire such that the force exerted on the end effector by the actuation wire and the compensation wire is the same.

The force balancing mechanism seeks to ensure that the shaft of the instrument and/or the end effector is not adversely affected by the actuation of the instrument. In one aspect, as the actuation wire is disposed off-centre with respect to the central axis of the shaft, there can be a tendency for the actuation wire to exert a bending moment on the shaft, causing an unwanted deflection of the shaft. However, in the current arrangement, as the actuator is moved, not only the actuation wire but also the compensation wire is moved. The compensation wire exerts a force on the end effector to compensate for any tendency for the actuation wire to cause the shaft to deflect due to the actuation wire not being located along the central axis of the shaft. Preferably, the actuation wire and the compensation wire are equally spaced from the central axis of the shaft, on opposite sides thereof. In this way, the compensation wire exerts an equal force to the actuation wire, but with an opposite rotational bending moment, counteracting any bending moment exerted by the actuation wire.

In another situation, the shaft of the instrument can be already subject to a desired deflection such that the shaft is in a curved configuration. In this way, the path length from the actuator to the end effector can be different as measured along actuation wire as compared with the path length via the compensation wire. The force balancing mechanism allows for relative movement therebetween, ensuring that this difference in path length does not cause an unwanted effect such as an inadvertent movement of the end effector.

In one convenient arrangement, the actuation wire is connected to the actuator by means of a push rod. The compensation wire is conveniently also connected to the actuator by its own push rod. The push rods transfer the movement of the actuator to the actuator wire and the compensation wire respectively. Regardless of whether or not push rods are involved, the force balancing mechanism is conveniently in the form of a rack and pinion structure connecting the compensation wire to the actuator. Conceivably, the actuation wire is also connected to the actuator by means of a structure including a rack and pinion. Where both the actuation wire and compensation wire are connected to the actuator by means of a structure including a rack and pinion, the pinion is preferably a single pinion common to both structures. In this way, the rack and pinion structure can transfer movement of the actuator into axial movement of the actuation and compensation wires, while allowing relative movement between the actuation and compensation wires in order to balance the forces applied by each wire. With such force balancing, the element of the end effector is moved from its first position to its second position without any deflecting of distorting forces being applied to the shaft or to the end effector. The term "actuation wire" is hereby meant to include any elongate structure capable of transferring movement from one end to the other, including cables, and even more solid transfer structures such as push rods or linkages.

According to one convenient arrangement, the at least one movable element of the end effector comprises a jaw movable between open and closed positions. Conceivably, the at least one movable element of the end effector comprises a pair of jaws, both jaws being movable between open and closed positions. In this arrangement, the compensation wire can also double as an actuation wire for the second jaw member. Alternatively, the at least one movable element of the end effector comprises a needle electrode movable between deployed and retracted positions. Whether the movement of the end effector is to open and close one or more jaws, or to extend and retract a needle electrode or other component, the compensation wire ensures that any actuation does not cause an unwanted deflection or distortion of the end effector or shaft. The force balancing mechanism also allows for any path length differences between the actuation wire and compensation wire due to the bending of the shaft to be accommodated.

The actuation wire is offset from the central axis of the shaft, either because it is not possible to locate the actuation wire along the central axis, or because the central axis already carries another actuation wire. In some instruments, the end effector performs more than one manoeuvre, for example firstly to open and close one or more jaws, and secondly to extend and retract a cutting element such as a needle electrode. In such an instrument, it is feasible that one of the maneuvers is preformed using an actuation wire running along the central axis of the instrument shaft, which means that the other manoeuvre is performed by an actuation wire which must necessarily be offset from the central axis by a certain amount. The compensation wire ensures that the bending moment imparted by such an offset actuation wire does not result in an unwanted deflection or distortion of the shaft of the instrument.

DESCRIPTION OF THE DRAWINGS

The invention will now be further described, by way of example only, with reference to the accompanying drawings, in which:

FIG. 1 is a perspective view of the handle of a surgical instrument in accordance with the present invention, FIGS. 2A to 2F are side views of the electrosurgical instrument of FIG. 1, shown in different positions, FIGS. 3A to 3F are enlarged side views of the end effector of the electrosurgical instrument of FIGS. 2A to 2F, corresponding to the positions of the instrument in each case, FIGS. 4A to 4F are sectional side views corresponding to FIGS. 2A to 2F, FIG. 6 is a sectional plan view of the instrument of FIGS. 2A to 2F.

DESCRIPTION OF THE EMBODIMENT

Figure 4E:
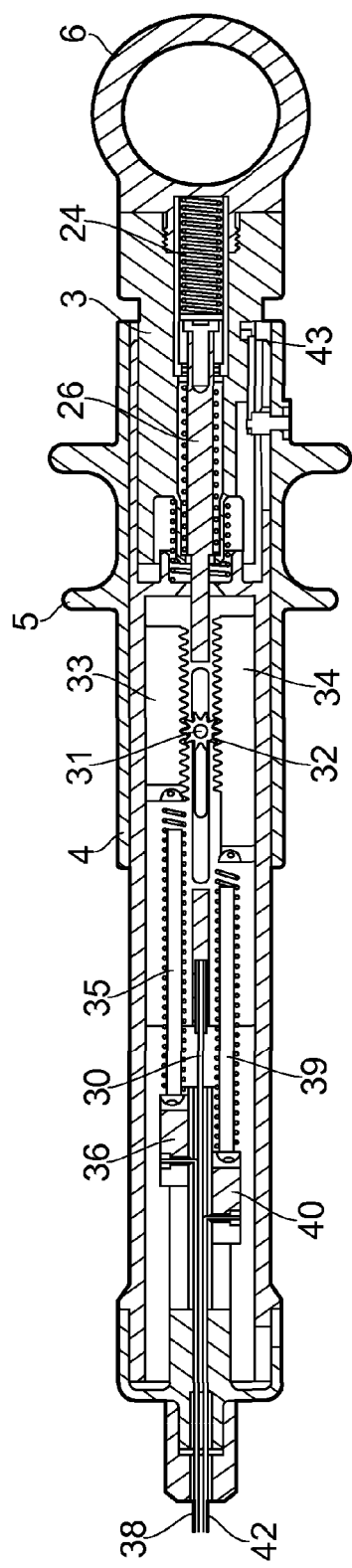

Referring to the drawings, FIG. 1 shows a handle for an endoscopic surgical instrument, the handle being shown generally at 1 and including a cylindrical housing 2 and a movable component in the form of a piston 3, the piston being slideable within the housing 2. A sleeve 4 is present on the housing 2, axially movable over the housing by means of a finger collar 5. A thumb ring 6 is present at the proximal end of the piston 3. By placing the fingers in the collar 5, and the thumb in the thumb ring 6, the user can firstly move the sleeve 4 over the housing 2, and subsequently, once a stop release button 11 has been activated, move the piston 3 into the housing 2. An elongate shaft 7 is present at the end of the housing 2, and an end effector shown generally at 8 is present at the distal end of the shaft 7.

Referring to FIGS. 2A to 2F, and 3A to 3F, FIG. 2A shows the handle 1 in a first position, in which the sleeve 4 is moved distally with respect to the thumb ring 6 and housing 2. As shown in FIG. 3A, the end effector 8 comprises a stationary jaw 9 and a movable jaw 10. With the sleeve 4 moved distally as shown in FIG. 2A, the movable jaw 10 is in its open position.

FIG. 2B shows the handle in a second position, in which the sleeve 4 is moved proximally causing the movable jaw 10 to close, as shown in FIG. 3B. Further proximal movement of the sleeve 4 is allowed until sleeve reaches a fully proximal position as shown in FIG. 2C. FIG. 2D shows the piston 3 being moved distally into the housing 2, which can only occur once the stop release button 11 has been activated. Moving the piston 3 into the housing 2 causes a needle electrode 12 to extend from the stationary jaw 9, as shown in FIG. 3D. Once the needle electrode 12 has been deployed, the piston 3 can be allowed to return slightly, under the action of a biasing mechanism to be described subsequently, such that it is held in a stable position by a latch mechanism, also to be described subsequently. This is the position shown in FIGS. 2E & 3E. To allow the piston 3 to move proximally and withdraw the needle electrode 12 back into the stationary jaw 9, the latch mechanism is disengaged by moving the piston distally into the housing (as shown in FIG. 2F) and then releasing it. The piston 3 and thumb ring 6 can then move proximally under the influence of the biasing mechanism to the position shown in FIGS. 2B & 3B.

FIGS. 4A to 4F show the internal components of the handle 1. The piston 3 is received in a cylindrical bore 13 within the housing 2, and biased into the retracted position by a first spring 14 located in the bore. The piston 3 itself has a cylindrical chamber 15, divided into three sections, each of successively decreasing diameter and delineated by shoulders 16 and 17 on the side wall of the chamber 15. A first proximal section 18 extends from a proximal end wall 19 to the first shoulder 16, while a second intermediate section 20 extends from the first shoulder 16 to the second shoulder 17. A third distal section 21 extends from the second shoulder 17 to a distal end wall 22 of the chamber 15. An aperture 23 is present in the distal end wall 22.

Present within the first section 18 is a second spring 24, constrained between the proximal end wall 19 and a washer 25, normally located against the first shoulder 16. Present within the second and third sections 20 & 21 is a push rod 26, the push rod having an end component 27, the end component being capable of bearing against the washer 25 in a proximal direction. A washer 60 is located on the push rod 26, limited for proximal movement by the first shoulder 16. A third spring 28 is present on the push rod 16, located between the washer 60 and the distal end wall 22 of the chamber 15.

The push rod 26 extends distally through the aperture 23 in the distal end wall 22, and extends along the central axis of the housing until it terminates in an end face 29. A needle actuation wire 30 is connected to the end face 29 of the push rod 26, the actuation wire 30 extending forwardly along the central axis of the housing until it reaches the needle electrode 12.

The sleeve 4 is slideably mounted on the housing 2 by means of a spindle 31 on which is mounted a pinion gear 32, cooperating with first and second rack gears 33 & 34 to form a double rack and pinion arrangement. The rack gears 33 & 34 are freely mounted within the push rod 26 (see FIG. 6) such that the push rod 26 can be moved longitudinally without causing a corresponding movement of the pinion gear 32 or rack gears 33 & 34. However, due to the fixed arrangement between the spindle 31 and the sleeve 4, longitudinal movement of the sleeve 4 causes a corresponding movement of the pinion gear 32, and hence the rack gears 33 & 34.

A spring 37 is connected between the rack gear 33 and a slider 36. A distally extending push rod 35 is located within the spring 37, and is maintained in contact with the slider 36 by the action of the spring 37. A jaw actuation wire 38 is attached to the slider 36, and extends distally to the movable jaw 10. In similar fashion, a spring 41 is connected between the rack gear 34 and a slider 40. A distally extending push rod 39 is located within the spring 41, and is maintained in contact with the slider 40 by the action of the spring 41. A force compensation wire 42 is attached to the slider 40, and extends distally to the stationary jaw 9.

To operate the surgical instrument, a user grips the handle 1 with fingers placed within the finger collar 5 and a thumb in the thumb ring 6. To open the movable jaw 10, the user pushes the finger collar distally in order to slide the sleeve 4 distally with respect to the thumb ring 6 and housing 2. This moves the spindle 31 distally, causing the pinion gear 32 to move the rack gear 33 distally. This results in the rack gear 33 pushing the push rod 35 and slider 36 distally, and also the jaw actuation wire 38. This allows the movable jaw 10 to open with respect to the stationary jaw 9, as shown in FIG. 3A. To close the jaw 10, the user pulls the finger collar 5 proximally, sliding the sleeve 4 proximally with respect to the thumb ring 6 and housing 2. This moves the spindle 31 proximally, causing the pinion gear 32 to move the rack gear 33 proximally. This results in the rack gear 33 pulling the spring 37 (and hence push rod 35 and slider 36) proximally, causing the jaw actuation wire 38 to be pulled against the jaw 10, moving it to a closed position as shown in FIG. 3B. The spring 37 controls the load applied to the jaw, and prevents overloading thereof.

As the jaw actuation wire 38 is offset from the central axis of the housing 2, pulling on the wire 38 imparts a bending moment to the end effector 8 which might cause the elongate shaft 7 to become deflected from the longitudinal axis. However, the proximal movement of the spindle 31 also causes the rack gear 34 to be moved proximally, causing the force compensation wire 42 to exert a compensating force on the end effector, due to the proximal movement of the spring 41, and hence push rod 39 and slider 40. As the force compensation wire 42 is offset from the central axis of the housing in the opposite sense to that of the jaw actuation wire 38, the force exerted by the wire 42 acts to counteract any tendency for the wire 38 to deflect the shaft 7. The dual rack and pinion arrangement of the pinion gear 32 and the rack gears 33 & 34 allows relative movement between the rack gears 33 & 34, so that the push rods 35 & 39 and sliders 36 & 40 can move to a position in which the forces on the shaft 7 are balanced.

Figure 4F:
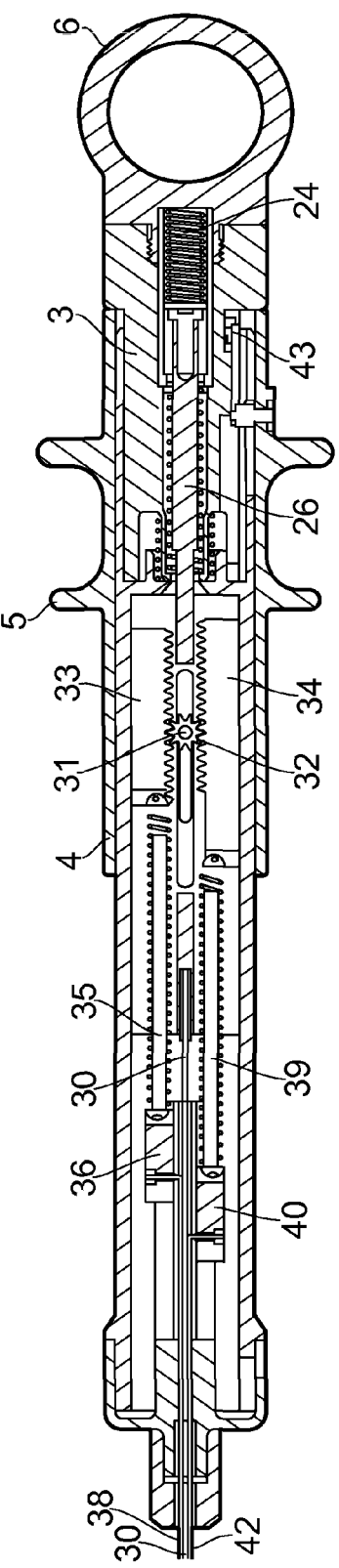
Figure 5:
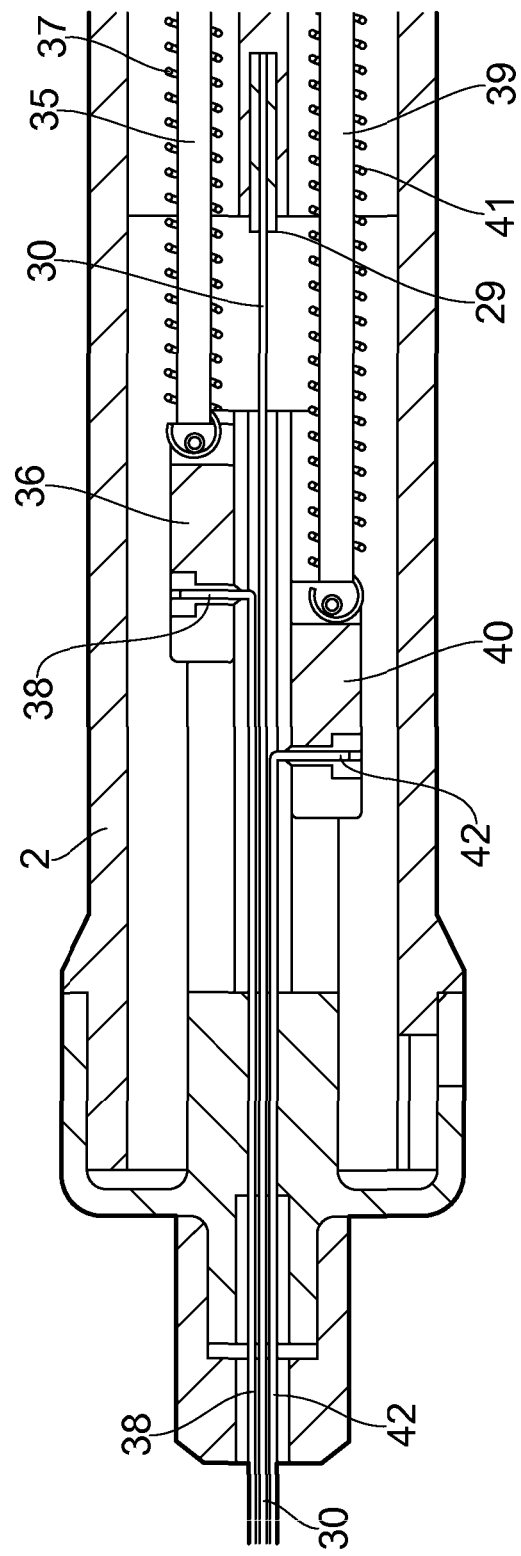
FIG. 5 is an enlarged sectional side view of the end of the handle of the electrosurgical instrument of FIGS. 1A to 1D.

To deploy the needle electrode 12 from the stationary jaw 9, the user pushes the piston 3 into the housing 2 using the thumb ring 6. This can only be achieved when the sleeve 4 is in its fully proximal position (as shown in FIGS. 2C & 4C), meaning that the movable jaw 10 is in its closed position. The stop release button 11 must be depressed by the user to allow distal movement of the piston 3. As piston 3 moves distally, spring 14 is compressed. Further movement of piston 3 causes the washer 25 to push against the end face 27 of push rod 26 and move push rod 26 distally. This results in the needle electrode 12 being extended from the stationary jaw 9. Further movement of the piston 3 compresses the spring 24 limiting the load which can be applied to the needle electrode 12. FIGS. 2D & 4D show the needle electrode 12 in its fully extended position. The user may then release the piston 3 and allow it to be held in position by a latch mechanism 43, which operates to hold the piston in place as shown in FIGS. 2E & 4E. To release the latch mechanism 43, the user once again pushes the piston 3 distally (as shown in FIGS. 2F & 4F) which releases the latch mechanism and allows the piston 3 to move proximally under the influence of the spring 14, back to the position shown in FIGS. 2C & 4C.

The handle 1 described above is used to cause selective opening and closing of a jaw mechanism, and also the deployment and retraction of a needle electrode. However, the handle can also be used for other types of instrument, such as a cutting forceps instrument. In this arrangement the actuation wire 38 once again governs the opening and closing of one or more jaws, and the actuation wire 30 causes the reciprocal axial movement of a mechanical cutting blade. In this way it can be seen that the handle mechanism can be used for a variety of different purposes, while the force compensation mechanism ensures that unwanted deflection of the shaft of the instrument does not occur. This is particularly important where the instrument is an endoscopic instrument, where the shaft may be a meter or more in length and somewhat susceptible to deflection at the tip. The force balancing mechanism also compensates for the difference in path lengths for the actuation wires that occurs when the shaft is curved rather than straight. Similarly, other finger and thumb grip constructions can be envisaged, without departing from the scope of the present invention.

The invention claimed is:

1. An electrosurgical instrument for the treatment of tissue, the electrosurgical instrument comprising:
   a longitudinal instrument shaft having a central axis, a proximal end and a distal end;
   an end effector at the distal end of the longitudinal instrument shaft, the end effector comprising at least one element movable between a first and a second position;
   an actuator including a handle capable of reciprocating movement between a first actuator position and a second actuator position;
   an actuation wire associated with the actuator for movement therewith and being connected to the end effector such that movement of the actuator causes the actuation wire to move the at least one element between its first and second positions, the actuation wire running longitudinally of the longitudinal instrument shaft and being offset on one side from the central axis of the longitudinal instrument shaft;
   a compensation wire also associated with the actuator and connected to the end effector, the compensation wire running longitudinally of the longitudinal instrument shaft and being offset on the opposite side of the central axis of the longitudinal instrument shaft to that of the actuation wire; and
   a force balancing mechanism allowing relative movement between the actuator and both the actuation wire and the compensation wire, such that a force exerted on the end effector by the actuation wire and the compensation wire is the same,
   wherein the force balancing mechanism includes a single pinion and two racks for connecting the compensation wire to the actuator, and wherein the actuator is directly connected to the single pinion.

2. The electrosurgical instrument according to claim 1, wherein the actuation wire and the compensation wire are equally spaced from the central axis of the shaft, on opposite sides thereof.

3. The electrosurgical instrument according to claim 1, wherein the actuation wire is connected to the actuator by means of a push rod.

4. The electrosurgical instrument according to claim 1, wherein the compensation wire is connected to the actuator by means of a push rod.

5. The electrosurgical instrument according to claim 1, wherein the at least one movable element of the end effector comprises a jaw movable between open and closed positions.

6. The electrosurgical instrument according to claim 5, wherein the at least one movable element of the end effector comprises a pair of jaws movable between open and closed positions.

7. The electrosurgical instrument according to claim 6, wherein the actuation wire is connected to one jaw, and the compensation wire is connected to the other jaw, so as to act as an additional actuation wire.

8. The electrosurgical instrument according to claim 1, wherein the at least one movable element of the end effector comprises a needle electrode movable between deployed and retracted positions.

\* \* \* \* \*